United States Patent [19]

Saxinger et al.

[11] Patent Number: 4,661,445
[45] Date of Patent: Apr. 28, 1987

[54] COMPETITIVE ELISA FOR THE DETECTION OF HTLV-III ANTIBODIES

[76] Inventors: W. Carl Saxinger, 6814 Renita La., Bethesda, Md. 20817; Robert C. Gallo, 8513 Thornden Terr., Bethesda, Md. 20814

[21] Appl. No.: 737,458

[22] Filed: May 24, 1985

[51] Int. Cl.$^4$ ............................................. G01N 33/53
[52] U.S. Cl. ............................................. 435/7; 435/5; 435/810; 436/518; 436/528; 436/543; 436/808; 436/809; 436/811; 436/825; 935/110
[58] Field of Search ............ 435/5, 7, 810; 436/518, 436/528, 543, 808, 809, 811, 825; 935/110

[56] References Cited

U.S. PATENT DOCUMENTS 4,520,113  5/1985  Gallo ........................................ 435/5

FOREIGN PATENT DOCUMENTS 0136798  4/1985  European Pat. Off. .................. 435/7
0138667  4/1985  European Pat. Off. ............ 436/808
0130196  7/1984  Japan ....................................... 435/4

OTHER PUBLICATIONS

Chemical Abstracts 103: 118450v, Casey (1985).
Kalyanaraman, Virology, 32, pp. 61–70 (1984).
Wisdom, Clinical Chemistry, 22(8), pp. 1243–1244 (1976).
Yolken, Reviews of Infectious Diseases, 4(1), pp. 35, 47, 48, 49 (1982).

Primary Examiner—Christine M. Nucker
Assistant Examiner—Robert Benson
Attorney, Agent, or Firm—John S. Roberts, Jr.

[57] ABSTRACT

A competitive enzyme-linked immunosorbent assay (ELISA) for the detection of antibodies is disclosed. This ELISA technique is more sensitive, more specific, and more accurate than known ELISA techniques. The competitive ELISA of this invention is particularly suited to the detection of human T-cell leukemia-lymphoma virus type III (HTLV-III). Antigenic or viral fragments are bound to a solid support. The bound fragments are then incubated with a heterologous antiserum which binds to the bound fragments. Test sera is then added to the bound fragments and tested for absorbance.

2 Claims, No Drawings

COMPETITIVE ELISA FOR THE DETECTION OF HTLV-III ANTIBODIES

BACKGROUND AND GENERAL DESCRIPTION

The present invention is a specific and sensitive method of detecting antibodies in test sera. The method, competitive enzyme-linked immunosorbent assay (ELISA), was developed, in particular, for the detection of human T-cell leukemia-lymphoma virus type III (HTLV-III), the putative causative agent of acquired immune deficiency syndrome (AIDS). This method, however, is generally applicable to the HTLV family of viruses, as well as other antigens and their corresponding antibodies.

Many immunoassay techniques exist for the immunosurveilance of antigens and antibodies. The indirect ELISA assay and the "Western" electroblotting assays are among the most sensitive. However, one of the drawbacks of these procedures is the background interference caused by nonimmune immunoglobulin and other serum factors present in all normal sera. This background, by its tendency to overlap and obscure low levels of specific reactive immunoglobulin, decreases the sensitivity of the assay and creates the need for supplementary confirmation tests in order to demonstrate true positivity. One such confirming test used extensively is the "Western" blotting procedure which, although sensitive, more specific, and informative for distinct viral proteins, is highly labor intensive, difficult to interpret, and is qualitative in nature (rather than quantitative).

The competitive ELISA immunoassay of the present invention greatly increases the sensitivity, specificity, and convenience of obtaining serologic data. The method increases sensitivity of specific antibody measurements by decreasing the background of normal immunoglobulin. The method increases specificity by the use of heterologous antiserum prepared against a virus, thus competitively blocking human specific antibodies.

The present invention is particularly suited to the detection of HTLV-III antibodies. Since AIDS and HTLV-III are known to be transmitted by blood products, a method for detecting contamination with HTLV-III is needed to guarantee the safety of recipients. Such a method should be as sensitive and specific as possible and also easily performed in a routine environment. Tests for viral markers such as reverse transcriptase, viral antigens, or nucleic acid sequences in fresh or cultured blood cells are slow and presently not suitable for large-scale screening. On the other hand, serological tests for viral antibodies or antigens are well suited for this purpsoe, since HTLV-III infected individuals are usually seropositive for antibodies to one or more HTLV-III proteins.

Statement of Deposit

HTLV-III was deposited in the American Type Culture Collection for a term of at least thirty years or five years after the last sample request, whichever is longer. These deposits were as follows:

| | |
|---|---|
| ATCC No. CRL 8602 | August 15, 1984 |
| ATCC Nos. 40125, 40126, 40127 | July 30, 1984 |
| ATCC No. CRL 8543 | April 19, 1984 |

SPECIFIC DISCLOSURE

Enzyme-linked immunosorbent assays (ELISA), in general, are performed by binding a reference reagent (antigen) to a solid phase support. Test sera, mixed with a labeled reagent, is then reacted with the bound reference reagent. The reagents then undergo a series of dilution, incubation, and washing steps in order to separate bound and free reagents. The process concludes with a detection step, compatible with the type of label used, designed to indirectly measure the amount of antibody (or antigen) in the test sera.

The above-described ELISA system is usually time consuming and, in the case of AIDS testing, occasionally produces false-positive results. Generally, antigen or virus fragments are bound to a solid support. The bound fragments are then incubated with heteroantiserum which binds to the bound fragments. Test sera is then added to the bound fragments and tested for absorbance. Suppression of absorbance by greater than 50 percent (relative to normal human serum) is considered a positive test result. The following description, using HTLV-III as the antigen, more specifically describes the present invention.

HTLV-III antigens are purified by rate-zonal ultracentrifugation, disrupted, and coated in the wells of microtiter plates. Test sera is tested and confirmed by a confirmatory neutralization screening which included an additional 2-hour incubation period before the test sample was incubated with the antigen-coated wells. During this extra 2 hours of incubation, the wells are exposed to unlabeled sheep antibody (heteroantiserum) to HTLV-III which reacts with and saturates HTLV antigen sites on the well, thus preventing the test serum from attaching to the well in the subsequent step. As a control in the test, adjacent wells are exposed to normal sheep serum during the additional incubation period. The preferred dilution of sheep antiserum is 1:2 at a titer of 10,000 or more. Sheep antiserum showing reactivity with proteins from phytohemagglutinin (PHA)-stimulted human lymphocyte preparations coated on microtiter plate wells are absorbed with PHA lymphocyte preparations until the reactivity is removed. The sheep antiserum used in this process requires absorption with one volume of cell equivalents per three volumes of serum to reach the end point. A suppression of the absorbance by >50 percent in the sample exposed to the unlabeled sheep antiserum to HTLV-III, relative to a standard normal human serum, is considered a positive confirmatory result for the presence of antibody to HTLV-III.

Preparation of sheep anti-HTLV-III

Sheep are inoculated intradermally with 1 mg of viral proteins in complete Freund's adjuvant (incomplete Freund's is used thereafter). The protein fraction is obtained by disruption of sucrose gradient purified HTLV-III/H9 virions in nonionic detergent and 0.6M NaCl. At the same time 1 mg of purified virions fixed in 0.04% paraformaldehyde is administered intradermally. Booster inoculations spaced 1 month apart are administered intradermally, intramuscularly or intravenously until titers are sufficiently high. Material for applying the test is obtained a liter at a time by plasmapheresis. Plasma from nonimmune sheep is obtained by the same procedure.

Western blotting comparative analyses performed use a three-layer immunoperoxidase procedure.

While the protein fraction noted above is obtained by disruption of HTLV-III/H9 virions, practitioners in the art will understand that the invention also includes (but is not limited to) the use of purified viral protein, core antigens, and cloned subgenomic fragment derivatives. Based on the disclosure, many other modifications and ramifications will naturally suggest themselves to those skilled in the art. These alterations are intended to be within the scope of this invention.

The present invention may be practiced by use of a test kit which includes but is not limited to an insoluble porous surface or solid substrate, said surface or substrate preferably containing microtiter wells; a reagent containing an antigen or antibody to be bound to the insoluble surface or support; test sera; heteroantiserum which specifically binds to and saturates the antigen or antibody bound to the surface; and biologically suitable washing, incubating, and purifying reagents known to those skilled in the art.

EXAMPLE 1

Specific antibody determinations in chimpanzees experimentally inoculated with AIDS plasma Three chimpanzees (CH132, CH114, CH133) were inoculated with AIDS plasma and one (CH140) was inoculated only with normal human plasma. Blood was sampled biweekly from each animal and serum was tested in the standard indirect ELISA test for HTLV-III antibodies. A P/N value of >5 is considered by many to indicate positive reactivity. By this criterion all four of the animals were positive for passively transferred HTLV-III antibody reactivity. CH114 and CH133 also showed active production of HTLV-III antibodies beginning six to eight weeks after the infusion of AIDS plasma. When subjected to the antibody blocking procedure using sheep anti-HTLV-III, it was seen that the animal infused with normal human plasma (CH140) had a false positive reaction (there was no difference between blocking with immune or nonimmune sheep antiserum) and was therefore negative for antibodies to HTLV-III. The confirmatory test showed that all of the remaining samples were specifically positive for HTLV-III antibodies which were either passively transferred or actively produced. Additional positive and negative human control were also tested with the appropriate expected result (Table 1).

EXAMPLE 2

Comparison of sensitivities of antibody detection by indirect ELISA, Western blotting, and the competitive ELISA procedures Two positive AIDS sera were subjected to serial 3-fold dilutions in a normal negative serum. The use of negative serum as diluent provided a constant negative background. Conditions were adjusted so that the starting concentrations of positive antibodies in each positive series were about the same. In addition, false positive sera were created by "spiking" a normal negative serum with normal negative human IgG to give IgG concentrations three times and ten times over the normal limits. The results in Table 2 indicate that using the usual criteria of a P/N >5 "Western" blotting is approximately 10-fold more sensitive than the standard indirect ELISA test, while the present test is approximately 10-fold more sensitive than the "Western" blotting procedure. The "false-positive" sera would have been scored as positive by the indirect ELISA procedure but were scored as negative by both the "Western" blotting procedure and the present competitive ELISA procedure.

EXAMPLE 3

Comparison of the indirect ELISA, "Western" blotting, and competitive ELISA procedures for determination of HTLV-III antibodies in normal donor and AIDS-risk donor sera Sera were tested by indirect ELISA screening for sera with HTLV-III antibody reactivities with a P/N greater than the mean +1.5 standard deviations (P/N >3). These samples were then confirmed by the "Western" blotting procedure to identify sera reactive with verified HTLV-III protein bands. The same group of sera were retested using the competitive ELISA procedure. There was perfect concordance between the two tests for negative normal blood donors and positive asymptomatic homosexual males (AIDS-risk). In addition, 5 donors questionable by "Western" blotting were resolved into 2 positives and 3 negatives, by competitive ELISA test. Two of the 248 "Western" blot negative AIDS-risk sera were weakly positive, and 10 samples which were questionable by "Western" blot were all negative by competitive ELISA test. See Table 3.

EXAMPLE 4

Distribution of HTLV-I antibody among African donors

An indirect ELISA microtest to detect serum antibodies was used. Briefly, HTLV-I was purified by ratezonal ultracentrifugation, disrupted, and coated into the wells of microtiter plates. Portions (5 μl) of test sera, control positive sera, and control negative human sera were incubated overnight at 4° C. in wells containing 100 μl of 20 percent heat-inactivated normal goat serum and were quantitated by measurement of absorbance at 490 nm after reaction with peroxidase-labeled goat antiserum to human IgG. Sera with absorbance values two times greater than the normal control level were verified primarily by confirmatory neutralization which involved the same procedure as the screening test but included an additional 2-hour incubation period before the test sample was incubated with the antigen-coated wells. During this extra 2 hours of incubation, the wells were exposed to unlabeled sheep antibody to HTLV-I which reacted with and saturated HTLV antigen sites on the well, thus preventing the test serum from attaching to the well in the subsequent step. As a control in the test, adjacent wells were exposed to normal sheep serum during the additional incubation period. Sheep antiserum was used at a dilution of 1:2 and had a titer of 100,000 or more. Sheep antiserum showing reactivity with proteins from phytohemagglutinin (PHA)-stimulated human lymphocyte preparations coated on microtiter plate wells were absorbed with PHA lymphocyte preparations until the reactivity was removed. The sheep antiserum used in these experiments required absorption with one volume of cell equivalents per three volumes of serum to reach the end point. A suppression of the absorbance by >50 percent in the sampale exposed to the unlabeled sheep antiserum to HTLV-I, relative to a standard normal human serum was considered a positive confirmatory result for the presence of antibody to HTLV-I. Sera failing the confirmatory test were absorbed with detergent-released cytosols prepared from PHA-stimulated normal human lymphocytes and with HTLV-I-producing cells and retested for binding to HTLV-I. Samples were scored positive if the difference between absorption with virus-positive and -negative cell preparations was >50 percent. Titers of positive sera were determined by serial dilution, regression analysis of the titration curves, and solving for the dilution giving results equivalent to a 1:20 dilution of the reference negative control serum tested in wells of the same plate. In Table 4, R is the ratio of the sample to the negative control; all groups followed log-normal distributions of R.

TABLE 1

Confirmatory Blocking of Anti-HTLV-III Sera With Sheep Anti-HTLV-III Heteroantisera

| | P/N ELISA Absorbance Ratio | |
|---|---|---|
| Specimen No. | With Normal Sheep Serum | With anti-HTLV-III |
| Chimp 132 post AIDS inoculum | | |
| Passive antibody | 16.31 | 6.96 |
| Chimp 114 post AIDS inoculum | | |
| Passive antibody | 18.25 | 7.84 |
| Active antibody | >20 | 4.51 |
| Chimp 133 post AIDS inoculum | | |
| Passive antibody | 12.34 | 5.07 |
| Active antibody | >20 | 12.11 |
| Chimp 140 post control inoculum | | |
| Passive antibody | 9.16 | 9.16 |
| Positive Control Serum | >20 | 9.16 |
| Positive Control Serum | 11.25 | 3.39 |
| Negative Control Serum | .90 | 1.05 |

TABLE 2

Comparison of Sensitivities of HTLV-III Antibody Detection by Indirect ELISA, competitive ELISA and Western Blot Procedures

| Sample | Titer | ELISA (P/N) | Competitive Elisa (P/N) | Western Blot |
|---|---|---|---|---|
| W8539 | 18000. | 12.80+ | 0.79− | + |
| | 6000. | 11.49+ | 0.50+ | + |
| | 2000. | 9.64+ | 0.22+ | + |
| | 666. | 6.34+ | 0.13+ | + |
| | 222. | 4.26+− | 0.12+ | + |
| | 74. | 3.28+− | 0.08+ | + |
| | 25. | 1.59− | 0.13+ | +− |
| | 8. | 9.93− | 0.26+ | +− |
| | 2.7 | 1.21− | 0.49+ | − |
| | 0.9 | 1.15− | 0.59+ | − |
| | 0.3 | 1.03− | 1.10− | − |
| | 0.1 | 1.08− | 1.32− | − |
| S0137 | 18000. | 12.27+ | 0.50+ | + |
| | 6000. | 9.61+ | 0.26+ | + |
| | 2000. | 9.02+ | 0.16+ | + |
| | 666. | 6.46+ | 0.09+ | + |
| | 222. | 5.18+ | 0.07+ | + |
| | 74. | 3.28+− | 0.12+ | + |
| | 25. | 2.75− | 0.12+ | +− |
| | 8. | 1.82− | 0.22+ | +− |
| | 2.7 | 1.14− | 0.35+ | − |
| | 0.9 | 1.19− | 0.78− | − |
| | 0.3 | 1.07− | 1.23− | − |
| | 0.1 | 0.96 − | 1.55− | − |
| S1421 | false + | 12.60+ | 1.30− | − |
| S1422 | false + | 13.23+ | 1.70− | − |

TABLE 3

Comparison of Western Blot and Competitive ELISA Test Results: Normal Blood Donors and Asymptomatic Homosexual Males

| | | ELISA | | |
|---|---|---|---|---|
| | | − | + | +/− |
| Normal Blood Donors Western Blot | | | | |
| Negative | 352 | 352 | 0 | 0 |
| Positive | 0 | NA | NA | NA |
| ? | 5 | 3 | 2 | 0 |
| Asymptomatic Homosexual Males Western Blot | | | | |
| Negative | 248 | 246 | 0 | 2 |
| Positive | 65 | 0 | 65 | 0 |
| ? | 10 | 10 | 0 | 0 |

TABLE 4

Distribution of HTLV-I Antibody Among African Donors

| Geographic and Racial Background of Donors | Group Characteristics | Number Tested | R Median | Number With R> >2 | Number Positive |
|---|---|---|---|---|---|
| Egypt, white | Infectious disease clinic | 101 | 0.90 | 12 | 2 |
| Tunisia, white | Malignant lymphoma | 22 | 1.31 | 7 | 2 |
| | Mammary carcinoma | 256 | 2.10 | 136 | 6 |
| Ghana, black | Burkitt's patients | 610 | 3.32 | 336 | 52 |
| | Normal comparison population | 236 | 3.30 | 200 | 19 |
| Uganda, black | Burkitt's patients and normal comparison population | 86 | 1.71 | 31 | 18 |

TABLE 4-continued
Distribution of HTLV-I Antibody Among African Donors

| Geographic and Racial Background of Donors | Group Characteristics | Number Tested | R Median | Number With R> >2 | Number Positive |
|---|---|---|---|---|---|
| Nigeria, black | T-cell lymphoma | 9 | 1.60 | 2 | 2 |
| South Africa Cape Town, black and white | All donors | 283 | 0.90 | 38 | 15 |
| | Lymphoid malignancy | 22 | 0.86 | 2 | 1 |
| | Myeloid malignancy | 104 | 0.84 | 16 | 9 |
| | Solid tumors | 59 | 1.02 | 11 | 3 |
| | Nonmalignant disease and healthy blood donors | 98 | 0.80 | 9 | 2 |
| Johannesburg, black | Healthy blood donors | 104 | 0.9 | 5 | 0 |

We claim:

1. A method for the detection of HTLV-III antibodies in a test sample comprising
    coating microtiter plates with purified HTLV-III antigen to form antigen-coated wells;
    incubating a portion of said antigen coated wells with heterologous anti-HTLV-III;
    adding test sera to said wells;
    screening said wells for the amount of binding of HTLV-III antibodies by comparing said wells containing said heterologous anti-HTLV-III to control wells, said control wells being incubated without said heterologous anti-THLV-III.

2. A test kit for the detection of HTLV-III antibodies comprising in combination
    an insoluble surface or support containing microtiter wells;
    HTLV-III fragments which are bound to said support; and
    heterologous antiserum which specifically binds to said HTLV-III fragments; and
    means for detecting the amount of antibodies in a test sample which bind to said HTLV-III fragments.

* * * * *